United States Patent [19]

Yamaguchi et al.

[11] 4,271,180
[45] Jun. 2, 1981

[54] SYNERGISTIC MIXTURE OF THREE PYRETHROID SERIES INSECTICIDAL COMPOUNDS

[75] Inventors: Takashi Yamaguchi, Nishinomiya; Goro Shinjo; Yoshitoshi Okuno, both of Toyonaka, all of Japan

[73] Assignee: Sumitomo Chemical Company, Limited, Osaka, Japan

[21] Appl. No.: 58,159

[22] Filed: Jul. 17, 1979

[30] Foreign Application Priority Data

Jul. 19, 1978 [JP] Japan ................... 53/88854

[51] Int. Cl.³ .................... A01N 43/36; A01N 43/08; A01N 37/00; A01N 37/08
[52] U.S. Cl. ..................... 424/274; 424/40; 424/285; 424/306
[58] Field of Search ............... 424/306, 285, 40, 274

[56] References Cited

U.S. PATENT DOCUMENTS

| | | | |
|---|---|---|---|
| 3,702,891 | 11/1972 | Hamuro | 424/285 |
| 3,723,615 | 3/1973 | Okuno | 424/306 |
| 3,767,806 | 10/1973 | Rauch | 424/306 |
| 3,899,586 | 8/1975 | Okuno et al. | 424/40 |
| 3,906,089 | 9/1975 | Okuno et al. | 424/306 |
| 3,911,101 | 10/1975 | Okuno et al. | 424/306 |
| 3,934,023 | 1/1976 | Okuno et al. | 424/306 |
| 4,100,297 | 7/1978 | Grandadam et al. | 424/306 |

FOREIGN PATENT DOCUMENTS

| | | | |
|---|---|---|---|
| 116329 | 12/1969 | Denmark | 424/306 |
| 51-32728 | 3/1976 | Japan | 424/306 |

Primary Examiner—Douglas W. Robinson
Attorney, Agent, or Firm—Stevens, Davis, Miller & Mosher

[57] ABSTRACT

An insecticidal composition containing an inert carrier and as active ingredients an insecticidally effective amount of a mixture comprising 2-allyl-3-methylcyclopento-2-ene-1-one-4-yl 2',2',3',3'-tetramethylcyclopropanecarboxylate or 2-propargyl-3-methylcyclopento-2-ene-1-one-4-yl 2',2',3',3'-tetramethylcyclopropanecarboxylate, and 3-phenoxybenzyl chrysanthemate, 5-benzyl-3-furylmethyl chrysanthemate or 3-phenoxybenzyl 2',2'-dimethyl-3'-(2'',2''-dichlorovinyl)-cyclopropane-1'-carboxylate, and N-(3,4,5,6-tetrahydrophthalimido)methyl chrysanthemate, which has synergistic lethal and knock-down effect on harmful insanitary insects as well as a synergistic flushing-out effect on cockroaches particularly as oil sprays, emulsifiable concentrates and aerosols.

12 Claims, 4 Drawing Figures

RELATION BETWEEN THE MIXING RATIO OF THE (C)/(K)(30:70) MIXTURE TO THE COMPOUND (F) AND THE MORTALITY (RELATIVE EFFICACY) OF THE (C)/(K)/(F) MIXTURE ON HOUSEFLY.

RELATION BETWEEN THE MIXING RATIO OF THE (C)/(K)(30:70) MIXTURE TO THE COMPOUND (F) AND THE MORTALITY (RELATIVE EFFICACY) OF THE (C)/(K)/(F) MIXTURE ON HOUSEFLY.

RELATION BETWEEN THE MIXING RATIO OF THE (A)/(K)(25:75) MIXTURE TO THE COMPOUND (F) AND THE KNOCK-DOWN EFFECT OF THE (A)/(K)/(F) MIXTURE ON NORTHERN HOUSE MOSQUITO.

RELATION BETWEEN THE MIXING RATIO OF THE (A)/(K)(30:70) MIXTURE TO THE COMPOUND (F) AND THE MORTALITY OF THE (A)/(K)/(F) MIXTURE ON GERMAN COCKROACH.

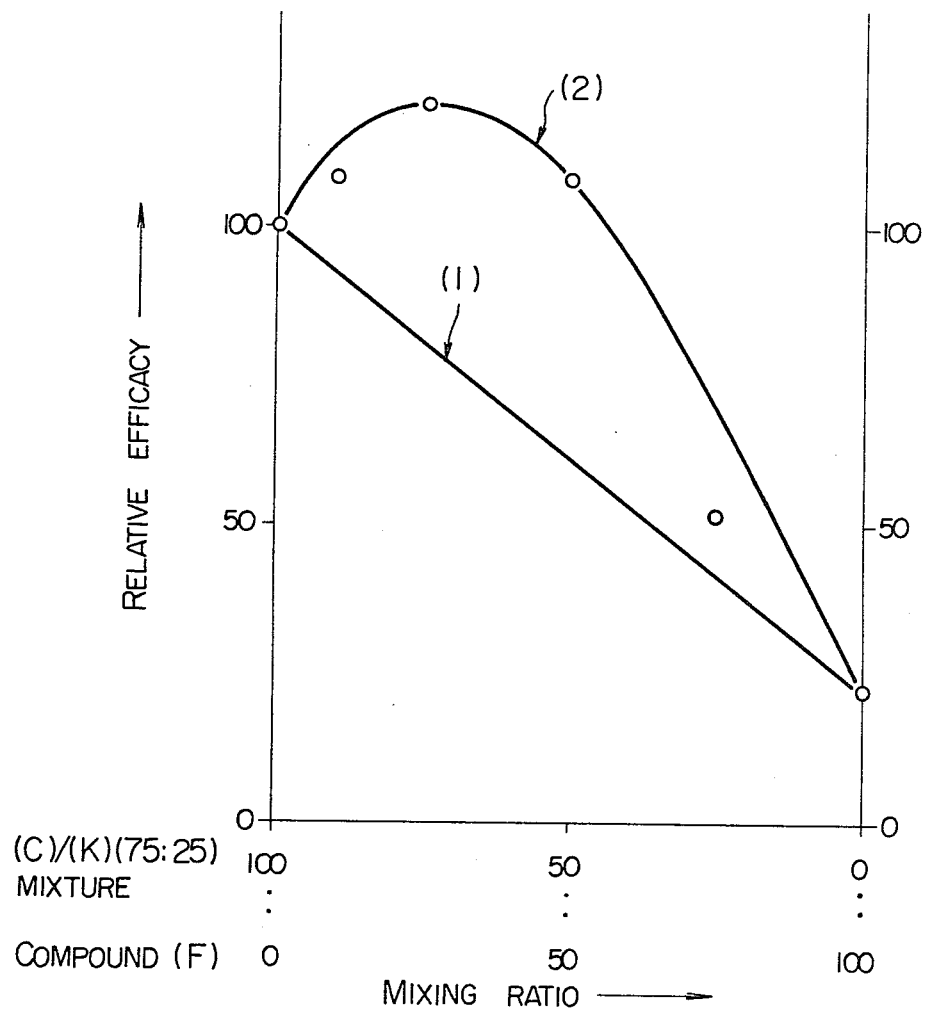

SYNERGISTIC MIXTURE OF THREE PYRETHROID SERIES INSECTICIDAL COMPOUNDS

The present invention relates to pyrethroid series insecticidal compositions which are very effective as an active ingredient for insecticidal spray agents such as oil sprays, emulsifiable concentrates and aerosols. More particularly, it relates to insecticidal compositions characterized by containing an inert carrier and as active ingredients, an insecticidally effective amount of a mixture comprising a pyrethroid series compound of the formula (I),

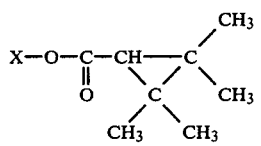

wherein X is

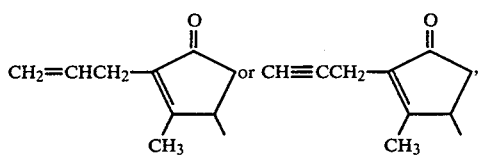

a pyrethroid series compound of the formula (II),

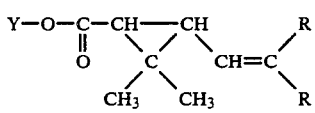

wherein when Y is

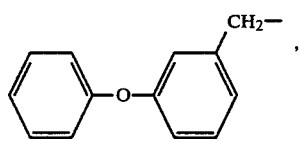

R is a methyl group or chlorine atom, and when Y is

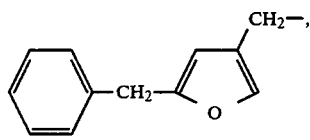

R is a methyl group, and a pyrethroid series compound of the formula (III),

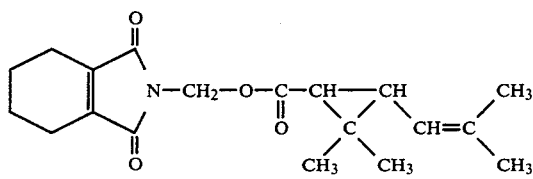

in a proper ratio.

In general, pyrethroid series insecticides are roughly divided into the so-called knock-down agent superior in a knock-down effect and the so-called killing agent superior in a lethal effect. Practically, it is required for the insecticides to have both of the effects, but at present there are not known single pyrethroid series insecticides having both effects and besides economical advantages.

In producing preparations used for controlling harmful insanitary insects in houses such as flies, mosquitoes and cockroaches, it is common to mix knock-down agent and a synergist (e.g. piperonyl butoxide) or a killing agent (e.g. DDVP) thereby giving both knock-down effect and lethal effect to the preparations.

Recently, there are increasing examples in which pyrethroid series insecticides are used as a mixture. It is however vary difficult to presume the combination of pyrethroid series insecticides showing a remarkable synergistic effect, and few examples in which such combination produces a synergistic effect are only disclosed in West German Pat. No. 1,642,339, U.S. Pat. Nos. 3,702,891, 3,723,615 and 3,899,586 and British Pat. No. 1,441,227.

For the reasons as described above, the inventors tried to obtain insecticidal compositions having a high insecticidal effect by making use of a remarkable synergistic effect obtained by proper mixing of different pyrethroid series insecticides. For this purpose, the inventors eagerly examined the biological activity of many pyrethroid series compounds and mixtures thereof against houseflies, mosquitoes and cockroaches for the presence of a synergistic effect. As a result, the inventors found that the mixtures of the pyrethroid series compounds of the present invention display a remarkable synergistic effect, showing an insecticidal effect and a flushing-out effect against cockroaches higher than expected. The inventors thus attained the present invention.

The insecticidal compositions of the present invention have such a rapdi knock-down effect and a high lethal effect against harmful insanitary insects (e.g. houseflies, mosquitoes, cockroaches) as not to be expected from the single component of the compositions.

Further, in controlling particularly cockroaches, it is desired for insecticides to have a high effect to flush cockroaches out of a hiding place (a flushing-out effect) in order to increase the opportunity of contact between cockroaches and the insecticides thereby remarkably increasing the insecticidal effect. The insecticidal compositions of the present invention have a superior flushing-out effect in addition to the foregoing knock-down effect and lethal effect.

The flushing-out effect of pyrethroids against cockroaches was already reported by P. R. Chadwick [International Pest Control (1976)]. G. Shinjo, M. Yoskida and Y. Okuno, the coinventors of this invention, also reported a study on this flushing-out effect in the 30th meeting (1978) of Japanese Sanitation and Animal Society. As is clear from these reports, the effect to flush cockroaches out of a hiding place has a characteristic of increasing the opportunity of contact between cockroaches and insecticides thereby remarkably increasing the effect of the insecticides.

In general, pyrethroid series compounds tend to be lacking in stability to light, heat and oxidation, and therefore, in the preparation of the mixed compositions of the present invention, the insecticidal effect of the compositions can be made more stable by adding as a stabilizer proper amounts of antioxidants or ultraviolet absorbers, for example phenol derivatives (e.g. BHT, BHA), bisphenol derivatives, arylamines (e.g. phenyl-α-naphthylamine, phenyl-β-naphthylamine, condensation products of phenetidine and acetone) or benzophenone compounds.

The present insecticidal composition may comprise 0.01 to 90% by weight of the above mentioned mixture as the active ingredients.

The chemical names, structures and physical properties of the pyrethroid series compounds of the formulae (I), (II) and (III) are as follows:

| Compound | Chemical name | Structure | Physical property |
|---|---|---|---|
| (A) | (±)-2-Allyl-3-methylcyclopento-2-ene-1-one-4-yl 2',2',3',3'-tetramethyl-cyclopropanecarboxylate | 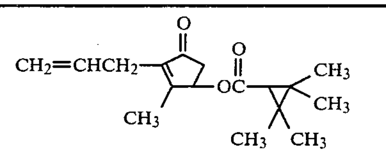 | $n_D^{23.6}1.4983$ |
| (B) | (+)-2-Allyl-3-methylcyclopento-2-ene-1-one-4-yl 2',2',3',3'-tetramethyl-cyclopropanecarboxylate | | $n_D^{24.0}1.4980$ |
| (C) | (±)-2-Propargyl-3-methylcyclopento-2-ene-1-one-4-yl 2',2',3',3'-tetramethylcyclopropanecarboxylate | 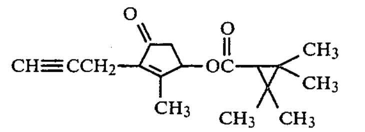 | $n_D^{24.0}1.5005$ |
| (D) | (+)-2-Propargyl-3-methylcyclopento-2-ene-1-one-4-yl 2',2',3',3'-tetramethyl-cyclopropanecarboxylate | | $n_D^{25.0}1.5001$ |
| (E) | 3-Phenoxybenzyl (±)-cis,trans-chrysanthemate | 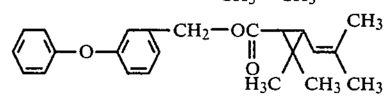 | $n_D^{23.0}1.5502$ |
| (F) | 3-Phenoxybenzyl (+)-cis,trans-chrysanthemate | | $n_D^{25.0}1.5487$ |
| (G) | 3-Phenoxybenzyl (+)-trans-chrysanthemate | | $n_D^{25.0}1.5482$ |
| (H) | 5-Benzyl-3-furylmethyl (±)-cis,trans-chrysanthemate | 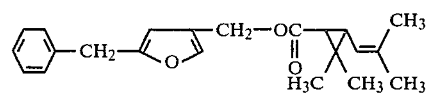 | m.p. 43°–48° C. |
| (I) | 5-Benzyl-3-furylmethyl (+)-cis,trans-chrysanthemate | | $n_D^{22.0}1.5305$ |
| (J) | 5-Benzyl-3-furylmethyl (+)-trans-chrysanthemate | | $n_D^{20.0}1.5345$ |
| (K) | N-(3,4,5,6-tetrahydrophthalimido)-methyl (±)-cis,trans-chrysanthemate | 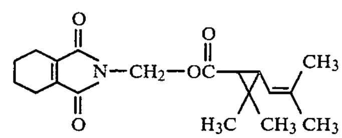 | m.p. 65°–80° C. |
| (L) | N-(3,4,5,6-tetrahydrophthalimido)-methyl (+)-trans-chrysanthemate | | $n_D^{25.5}1.5176$ |
| (M) | N-(3,4,5,6-tetrahydrophthalimido)methyl (+)-cis,trans-chrysanthemate | | $n_D^{23}1.5182$ |
| (N) | 3-Phenoxybenzyl (±)-cis,trans-2',2'-dimethyl-3'-(2'',2''-dichlorovinyl)cyclopropane-1'-carboxylate | 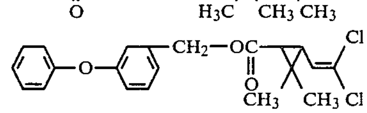 | $n_D^{24}1.5641$ |
| (O) | 3-Phenoxybenzyl (+)-trans-2',2'-dimethyl-3'-(2'',2''-dichlorovinyl)cyclopropane-1'-carboxylate | | $n_D^{22}1.5660$ |

Further, in formulating the present compositions, multi-purpose compositions having a stronger effect can be prepared by mixing other active ingredients such as synergists, insecticides other than pyrethroid, pyrethroid series insecticides other than those of the present invention and isomers thereof. The synergists include for example α-[2-(2-butoxyethoxy)ethoxy]-4,5-methylenedioxy-2-propyltoluene, N-(2-ethylhexyl)-bicyclo[2,2,1]hepta-5-ene-2,3-dicarboximide and octachlorodipropyl ether. The insecticides other than pyrethroid include for example Fenitrothion, Diazinon, BHC and DDVP. The pyrethroid series insecticides other than those of the present invention include for example (±)-2-allyl-3-methylcyclopento-2-ene-1-one-4-yl (±)-cis,trans-chrysanthemate.

In the present invention, the mixing ratio of the composition is obtained by mixing pyrethroid series compounds of the formulae (I) and (III) in a ratio of 95:5 to 5:95, and mixing this mixture with a pyrethroid series compound of the formula (II) in a ratio of 95:5 to 30:70, preferably 90:10 to 40:60.

The insecticidal compositions of the present invention are mainly used, as described above, for preparing liquid agents such as oil sprays, emulsifiable concentrates and aerosols. But they may be used, if necessary, for preparing mosquito coils, mat for electric fumigators, other fumigants and dusts.

The excellent insecticidal effect of the present insecticidal compositions will be illustrated in detail with reference to the following test examples. But, the present invention is not of course limited to these examples.

TEST EXAMPLE 1

Three grams of each of the compounds (A), (F), (H), (K) and (N) and mixtures (A)+(K), (K)+(F), (K)+(H), (K)+(N), (A)+(K)+(F), (A)+(K)+(H) and (A)+(K)+(N) and 10 g of an emulsifier [Atmos 300/Tween 80 (8:2) mixture: Atmos 300 and Tween 80 are registered trade marks of Atlas Chemical Co.] were dissolved in 87 g of a deodorized kerosene (Isopar M, a registered trade mark of ESSO Standard Co.) to obtain 100 g of a base liquid for aerosol.

Ten grams of the base liquid was placed in a pressure container for aerosol, and 50 g of ion exchange water was added thereto. After attaching a valve to the container, 40 g of LPG was charged therein through the valve to obtain 100 g of an aerosol (final concentration of the compounds was 0.3%).

The insecticidal effect of each aerosol against housefly (Musca domestica) was tested according to the CSMA Aerosol Test Method for Flying Insects (Soap and Chemical Specialties, Blue Book, 1965), and the results as shown in Table 1 were obtained. Further, with the (A)/(K)/(F) mixture, the relation between the mixing ratio and relatively efficacy [the mortality of the compound (A)/(K) (30:70) mixture was taken as 100] was obtained. The results are shown in Table 1.

TABLE 1

| Compound | Mixing ratio | Mortality (%) | Relative efficacy*1 |
|---|---|---|---|
| A:K | 30:70 | 76 | 100 |
| K:F | 75:25 | 77 | 101 |
| K:H | 75:25 | 78 | 103 |
| K:N | 75:25 | 82 | 108 |
| A | — | 48 | 63 |
| F | — | 88 | 116 |
| H | — | 90 | 118 |
| K | — | 52 | 68 |
| N | — | 91 | 120 |
| A:K:F*2 | 27:63:10 | 83 | 109 |
|  | 22.5:52.5:25 | 92 | 121 |
|  | 15:35:50 | 93 | 122 |
|  | 7.5:17.5:75 | 87 | 114 |
| A:K:H | 22.5:52.5:25 | 93 | 122 |
| A:K:N | 22.5:52.5:25 | 98 | 129 |

*1Relative efficacy = $\frac{\text{Mortality of the compounds other than (A) + (K)}}{\text{Mortality of (A) + (K)}} \times 100$

*2The ratio of (A) to (K) in the mixtures is 3:7.

It is apparent from the table that a synergistic effect is observed by mixing the compound (F), (H) or (N) with the (A)/(K).

TEST EXAMPLE 2

In the same manner as in Test example 1, the compounds (C), (F), (H), (K) and (N), and mixtures (C)+(K), (K)+(F), (K)+(H), (K)+(N), (C)+(K)+(F), (C)+(K)+(H) and (C)+(K)+(N) were each formulated into a 0.3% aerosol and tested for efficacy on housefly (*Musca domestica*). The results are shown in Table 2.

Further, with the (C)/(K)/(F) mixture, the relation between the mixing ratio and the relative efficacy [the mortality of the (C)/(K) (30:70) mixture was taken as 100] was obtained. The results are shown in FIG. 1.

TABLE 2

| Compound | Mixing ratio | Mortality (%) | Relative efficacy*1 |
|---|---|---|---|
| C:K | 30:70 | 59 | 100 |
| K:F | 75:25 | 77 | 131 |
| K:H | 75:25 | 78 | 132 |
| K:N | 75:25 | 82 | 139 |
| C | — | 40 | 68 |
| F | — | 88 | 149 |
| H | — | 90 | 153 |
| K | — | 52 | 88 |
| N | — | 91 | 154 |
| C:K:F*2 | 27:63:10 | 67 | 114 |
|  | 22.5:52.5:25 | 79 | 134 |
|  | 15:35:50 | 87 | 145 |
|  | 7.5:17.5:75 | 88 | 149 |
| C:K:H | 22.5:52.5:25 | 80 | 153 |
| C:K:N | 22.5:52.5:25 | 85 | 144 |

*1Relative efficacy = $\frac{\text{Mortality of the compounds other than (C) + (K)}}{\text{Mortality of (C) + (K)}} \times 100$

*2The ratio of (C) to (K) in the mixtures is 3:7.

It is apparent from the table that a synergistic effect is observed by mixing the compound (F), (H) or (N) with the (C)/(K) mixture.

TEST EXAMPLE 3

In the same manner as in Test example 1, the compound (F) and (K), and mixtures (A)+(K), (K)+(F) and (A)+(K)+(F) were each formulated into a 0.3% aerosol and tested for an efficacy on Northern house mosquito (*Culex pipiens pallens*). The results are shown in Table 3. Further, with the (A)/(K)/(F) mixture, the relation between the mixing ratio and the relative efficacy [the value of KT$_{50}$ of the (A)/(K) (25:75) mixture was taken as 100] was obtained. The result is shown in FIG. 2.

TABLE 3

| Compound | Mixing ratio | KT$_{50}$(min)*1 | Relative efficacy*2 |
|---|---|---|---|
| A:K | 25:75 | 5.0 | 100 |
| K:F | 75:25 | 8.1 | 61 |
| F | — | 14.0 | 36 |
| K | — | 7.4 | 68 |
| A:K:F*3 | 22.5:67.5:10 | 4.7 | 106 |
|  | 20.0:60.0:20 | 4.4 | 114 |
|  | 17.5:52.5:30 | 4.3 | 115 |
|  | 12.5:37.5:50 | 4.6 | 109 |
|  | 7.5:22.5:70 | 6.2 | 81 |
|  | 2.5:7.5:90 | 9.9 | 51 |

*1A time required for 50% of the mosquitoes to be knocked down.

*2Relative efficacy = $\frac{\text{KT}_{50} \text{ of (A) + (K)}}{\text{KT}_{50} \text{ of the compounds other than (A) + (K)}} \times 100$

*3The ratio of (A) to (K) in the (A)/(K)/(F) mixture is 1:3.

It is apparent from FIG. 2 that a remarkable synergistic knock-down effect on Northern house mosquito adults is observed by mixing the compound (F) with the (A)/(K) mixture.

TEST EXAMPLE 4

In the same manner as in Test example 1, the compounds (F), (H), (J), (K) and (N) and mixtures (C)+(K), (K)+(F), (K)+(H), (K)+(J), (K)+(N), (C)+(K)+(F), (C)+(K)+(H), (C)+(K)+(J) and (C)+(K)+(N) were each formulated into a 0.3% aerosol and tested for efficacy on Northern house mosquito (*Culex pipiens pallens*). The results are shown in Table 4.

TABLE 4

| Compound | Mixing ratio | KT$_{50}$(min)*1 | Relative efficacy*2 |
|---|---|---|---|
| C:K | 25:75 | 4.1 | 100 |
| K:F | 80:20 | 7.8 | 53 |
| K:H | 80:20 | 6.6 | 62 |
| K:J | 80:20 | 6.1 | 67 |
| K:N | 80:20 | 7.6 | 54 |
| F | — | 14.0 | 29 |
| H | — | 8.8 | 47 |
| J | — | 6.8 | 60 |
| K | — | 7.4 | 55 |
| N | — | 13.5 | 30 |
| C:K:F*3 | 22.5:67.5:10 | 4.0 | 103 |
|  | 20:60:2: | 4.1 | 100 |
|  | 12.5:37.5:50 | 5.2 | 79 |
|  | 7.5:22.5:70 | 6.8 | 60 |
| C:K:H | 20:60:20 | 4.2 | 98 |
| C:K:J | 20:60:20 | 4.0 | 103 |
| C:K:N | 20:60:20 | 4.3 | 95/ |

*1According to Tst example 3.

*2Relative efficacy = $\frac{\text{KT}_{50} \text{ of CC) + CK)}}{\text{KT}_{50} \text{ of the compounds other than (C) + (K)}} \times \phi$

*3The ratio of(C) to (K) in the mixture is 1:3.

It is apparent from the table that every mixture has a remarkable synergistic knock-down effect on Northern house mosquito.

TEST EXAMPLE 5

In the same manner as in Test example 1, the compounds (A), (F), (H), (J), (K), (N) and (O), and mixtures (A)+(K), (K)+(F), (K)+(H), (K)+(J), (K)+(N), (K)+(O), (A)+(K)+(F), (A)+(K)+(H), (A)+(K)+(J), (A)+(K)+(N) and (A)+(K)+(O) were each formulated into a 0.3% aerosol and tested for efficacy on German cockroach (*Blattella germanica*). The results are shown in Table 5. Further, with the (A)/(K)/(F) mixture, the relation between the mixing ratio and the relative efficacy [the mortality of the (A)/(K) (30:70) mixture was taken as 100] was obtained. The results are shown in FIG. 3.

TABLE 5

| Compound | Mixing ratio | Mortality (%) | Relative efficacy*1 |
| --- | --- | --- | --- |
| A:K | 30:70 | 65 | 100 |
| K:F | 75:25 | 56 | 86 |
| K:J | 75:25 | 75 | 115 |
| K:N | 75:25 | 68 | 105 |
| K:O | 75:25 | 75 | 115 |
| A | — | 66 | 102 |
| F | — | 78 | 120 |
| J | — | 93 | 143 |
| K | — | 13 | 20 |
| N | — | 85 | 131 |
| O | — | 94 | 145 |
| A:K:F*2 | 27:63:10 | 76 | 117 |
|  | 22.5:52.5:25 | 84 | 129 |
|  | 15:35:50 | 89 | 137 |
|  | 7.5:17.5:75 | 90 | 138 |
| A:K:J | 22.5:52.5:25 | 91 | 140 |
| A:K:N | 22.5:52.5:25 | 88 | 135 |
| A:K:O | 22.5:52.5:25 | 97 | 149 |

*1According to Test example 1.
*2The ratio of (A) to (K) in the mixtures is 3:7.

It is apparent from the table that a synergistic effect is observed by mixing the compound (F), (J), (N) or (O) with the (A)/(K) mixture.

TEST EXAMPLE 6

0.3 Gram of each of the compounds (A), (F), (H), (J), (K), (N) and (O) and mixtures (A)+(K), (K)+(F), (K)+(H), (K)+(J), (K)+(N), (K)+(O), (A)+(K)+(F), (A)+(K)+(H), (A)+(K)+(J), (A)+(K)+(N) and (A)+(K)+(O) was accurately weighed and completely dissolved in 100 ml of a deodorized kerosene (Isopar M, a registered trade mark of ESSO Standard Co.) to obtain a 0.3% oil spray. The flushing-out effect of each oil spray on German cockroach (*Blattella germanica*) was tested by the following method.

The day before the test, a trigonal prism-like veneer shelter (side 3 cm, height 15 cm) in which 10 German cockroaches (ratio of male to female 1:1) were liberated, was placed at the center of the bottom of a glass chamber [70 cm×70 cm×70 cm (high)]. 4.2 Milliliters of the oil spray was sprayed into the glass chamber by means of a spray gun, and the number of cockroaches running out of the shelter was counted with the lapse of time for 10 minutes. The test results are shown in Table 6.

TABLE 6

| Compound | Mixing ratio | $FT_{50}$(min)*1 | Relative efficacy*2 |
| --- | --- | --- | --- |
| A:K | 25:75 | 2.2 | 100 |
| K:F | 75:25 | 3.1 | 71 |
| K:H | 75:25 | 3.2 | 69 |
| K:J | 75:25 | 3.0 | 73 |
| K:N | 75:25 | 3.0 | 73 |
| K:O | 75:25 | 2.7 | 81 |
| A | — | 5.9 | 37 |
| F | — | 5.4 | 50 |
| H | — | 5.9 | 37 |
| J | — | 4.2 | 52 |
| K | — | 3.0 | 73 |

TABLE 6-continued

| Compound | Mixing ratio | $FT_{50}$(min)*1 | Relative efficacy*2 |
| --- | --- | --- | --- |
| N | — | 3.0 | 73 |
| O | — | 2.6 | 85 |
| A:K:F*3 | 22.5:67.5:10 | 2.0 | 110 |
|  | 18.8:56.2:25 | 1.9 | 116 |
|  | 12.5:37.5:50 | 2.2 | 100 |
|  | 6.2:18.8:75 | 3.2 | 69 |
| A:K:H | 18.8:56.2:25 | 2.0 | 110 |
| A:K:J | " | 1.9 | 116 |
| A:K:N | " | 1.8 | 122 |
| A:K:O | " | 1.8 | 122 |

*1A time required for 50% of the cockroaches to be flushed out.
*2Relative efficacy $= \dfrac{FT_{50} \text{ of (A)} + \text{(K)}}{FT_{50} \text{ of the compounds other than (A)} + \text{(K)}} \times 100$
*3The ratio of (A) to (K) in the mixtures is 1:3.

It is apparent from the table that every mixture has a remarkable synergistic flushing-out effect on German cockroach.

TEST EXAMPLE 7

In the same manner as in Test example 6, the compounds (C), (F), (H), (K) and (N) and mixtures (C)+(K), (K)+(F), (K)+(H), (K)+(N), (C)+(K)+(F), (C)+(K)+(H) and (C)+(K)+(N) were each formulated into a 0.3% oil spray and tested for flushing-out effect on German cockroach (*Blattella germanica*). The results are shown in Table 7.

Further, with the (C)/(K)/(F) mixture, the relation between the mixing ratio and the relative efficacy [the $FT_{50}$ of the (C)/(K) (75:25) mixture was taken as 100] was obtained. The results are shown in FIG. 4.

TABLE 7

| Compound | Mixing ratio | $FT_{50}$(min)*1 | Relative efficacy*2 |
| --- | --- | --- | --- |
| C:K | 75:25 | 1.2 | 100 |
| K:F | 75:25 | 3.1 | 39 |
| K:H | 75:25 | 3.2 | 40 |
| K:N | 75:25 | 3.0 | 40 |
| C | — | 1.5 | 80 |
| F | — | 5.4 | 22 |
| H | — | 5.9 | 20 |
| K | — | 3.0 | 40 |
| N | — | 3.0 | 40 |
| C:K:F*3 | 67.5:22.5:10 | 1.1 | 109 |
|  | 56.2:18.8:25 | 1.0 | 120 |
|  | 37.5:12.5:50 | 1.1 | 109 |
|  | 18.8:6.2:75 | 2.3 | 52 |
| C:K:H | 68.5:22.5:10 | 1.1 | 109 |
|  | 56.2:18.8:25 | 1.1 | 109 |
|  | 37.5:12.5:50 | 1.3 | 92 |
|  | 18.8:6.2:75 | 2.2 | 55 |
| C:K:N | 56.2:18.8:25 | 1.1 | 109 |

*1According to Test example 6.
*2Relative efficacy $= \dfrac{FT_{50} \text{ of (C)} + \text{(K)}}{FT_{50} \text{ of the compounds other than (C)} + \text{(K)}} \times 100$
The ratio of (C) to (K) in the mixtures is 3:1.

It is apparent from the table that every mixture has a remarkable synergistic flushing-out effect on German cockroach.

TEST EXAMPLE 8

In the same manner as in Test example 6, the compounds (A), (F), (N), (H) and (L) and mixtures (A)+(L), (L)+(F), (L)+(N), (L)+(H), (A)+(L)+(F), (A)+(L)+(N) and (A)+(L)+(H) were each formulated into a 0.3% oil spray and tested for flushing-out effect on German cockroach (*Blattella germanica*). The results are shown in Table 8.

TABLE 8

| Compound | Mixing ratio | $FT_{50}$(min)*[1] | Relative efficacy*[2] |
|---|---|---|---|
| A:L | 25:75 | 2.0 | 100 |
| L:F | 75:25 | 2.4 | 83 |
| L:N | 75:25 | 2.3 | 87 |
| L:H | 75:25 | 2.6 | 77 |
| A | — | 5.9 | 34 |
| F | — | 5.4 | 41 |
| N | — | 3.0 | 73 |
| H | — | 5.9 | 34 |
| L | — | 2.4 | 83 |
| A:L:F*[3] | 18.8:56.2:25 | 1.9 | 105 |
| A:L:N | 22.5:68.5:10 | 2.0 | 100 |
|  | 18.8:56.2:25 | 1.8 | 111 |
|  | 12.5:37.5:50 | 1.9 | 105 |
|  | 6.2:18.8:75 | 2.4 | 83 |
| A:L:H | 18.8:56.2:25 | 1.9 | 105 |

*[1] According to Test example 6.

*[2] Relative efficacy = $\dfrac{FT_{50} \text{ of (A)} + \text{(L)}}{FT_{50} \text{ of the compounds other than (A) + (L)}} \times 100$

*[3] The ratio of (A) to (L) in the mixtures is 1:3.

It is apparent from the table that every mixture has a remarkable synergistic flushing-out effect on German cockroach.

TEST EXAMPLE 9

In the same manner as in Test example 6, the compounds (A), (F), (H), (M) and (N) and mixtures (A)+(M), (M)+(F), (M)+(H), (M)+(N), (A)+(M)+(N), (A)+(M)+(F) and (A)+(M)+(H) were each formulated into a 0.3% oil spray and tested for flushing-out effect on German cockroach (*Blattella germanica*). The results are shown in Table 9.

TABLE 9

| Compound | Mixing ratio | $FT_{50}$(min)*[1] | Relative efficacy*[2] |
|---|---|---|---|
| A:M | 25:75 | 2.2 | 100 |
| M:F | 75:25 | 2.5 | 88 |
| M:H | 75:25 | 2.7 | 81 |
| M:N | 75:25 | 2.4 | 92 |
| A | — | 5.9 | 37 |
| N | — | 3.0 | 73 |
| F | — | 5.4 | 41 |
| H | — | 5.9 | 37 |
| M | — | 2.5 | 88 |
| A:M:N | 22.5:67.5:10 | 1.9 | 116 |
|  | 18.8:56.2:25 | 1.8 | 122 |
|  | 12.5:37.5:50 | 1.9 | 116 |
|  | 6.2:18.8:75 | 2.5 | 88 |
| A:M:F | 18.8:56.2:25 | 2.0 | 110 |
| A:M:H | 18.8:56.2:25 | 2.1 | 105 |

*[1] According to Test example 6.

*[2] Relative efficacy = $\dfrac{FT_{50} \text{ of (A)} + \text{(M)}}{FT_{50} \text{ of the compounds other than (A) + (M)}} \times 100$

*[3] The ratio of (A) to (M) in the mixtures is 1:3.

It is apparent from the table that a remarkable synergistic flushing-out effect on German cockroach is observed by mixing the single compound (N), (F) or (H) with the (A)/(M) mixture.

Next, the preparation of the insecticidal compositions containing the pyrethroid series compounds of the formulae (I), (II) and (III) will be illustrated with reference to the following examples.

EXAMPLE 1

The compounds in Table 10 were each dissolved in methylchloroform to obtain 1 kg of the present insecticidal composition.

These insecticidal compositions were used as a base liquid in formulating aerosols and oil sprays.

TABLE 10

| Insecticidal composition | Amount (g) of the compounds in 1 kg of the insecticical composition | | |
|---|---|---|---|
|  | Compound (I) | Compound (II) | Compound (III) |
| 1 | (A) 100 | (E) 100 | (K) 300 |
| 2 | (A) 100 | (F) 100 | (K) 300 |
| 3 | (A) 100 | (H) 100 | (K) 300 |
| 4 | (A) 100 | (J) 100 | (K) 300 |
| 5 | (C) 100 | (E) 100 | (K) 300 |
| 6 | (C) 100 | (F) 100 | (K) 300 |
| 7 | (C) 100 | (H) 100 | (K) 300 |
| 8 | (C) 100 | (J) 100 | (K) 300 |
| 9 | (A) 100 | (G) 100 | (K) 300 |
| 10 | (A) 100 | (N) 100 | (L) 300 |
| 11 | (D) 100 | (O) 100 | (M) 300 |
| 12 | (C) 100 | (N) 100 | (K) 300 |
| 13 | (C) 100 | (O) 100 | (L) 300 |

EXAMPLE 2

The compounds in Table 10 were each mixed with 150 g of an emulsifier (Sorpol SM-200, a registered trade mark of Toho Kagaku Co.) and xylene to obtain 1 kg of the present emulsifiable concentrate.

EXAMPLE 3

The compounds in Table 11 were mixed with kerosene so that the total volume was 1 liter. The present oil sprays were thus obtained.

TABLE 11

| Insecticidal composition | Amount (g) of the compounds in 1 liter of the insecticidal composition | | |
|---|---|---|---|
|  | Compound (I) | Compound (II) | Compound (III) |
| 14 | (A) 1.0 | (F) 1.0 | (K) 3.0 |
| 15 | (A) 1.0 | (H) 1.0 | (K) 3.0 |
| 16 | (C) 1.0 | (F) 1.0 | (K) 3.0 |
| 17 | (C) 1.0 | (H) 1.0 | (K) 3.0 |
| 18 | (A) 1.0 | (N) 1.0 | (L) 3.0 |
| 19 | (A) 1.0 | (O) 1.0 | (M) 3.0 |
| 20 | (C) 1.0 | (N) 1.0 | (K) 3.0 |

EXAMPLE 4

Kerosene was added to the compounds in Table 11 so that the total volume was 500 ml. One hundred milliliters of the solution was placed in an aerosol container, and after attaching a valve to the container, 100 ml of LPG was charged therein through the valve to obtain the present aerosol.

BRIEF EXPLANATION OF THE DRAWINGS

FIG. 4 shows the flushing-out effect (relative efficacy) of the (C)/(K)/(F) mixture on German cockroach, in a relative efficacy-mixing ratio graph.

In FIGS. 1 to 4, (1) shows a theoretical value and (2) an experimental value.

Figure 1:
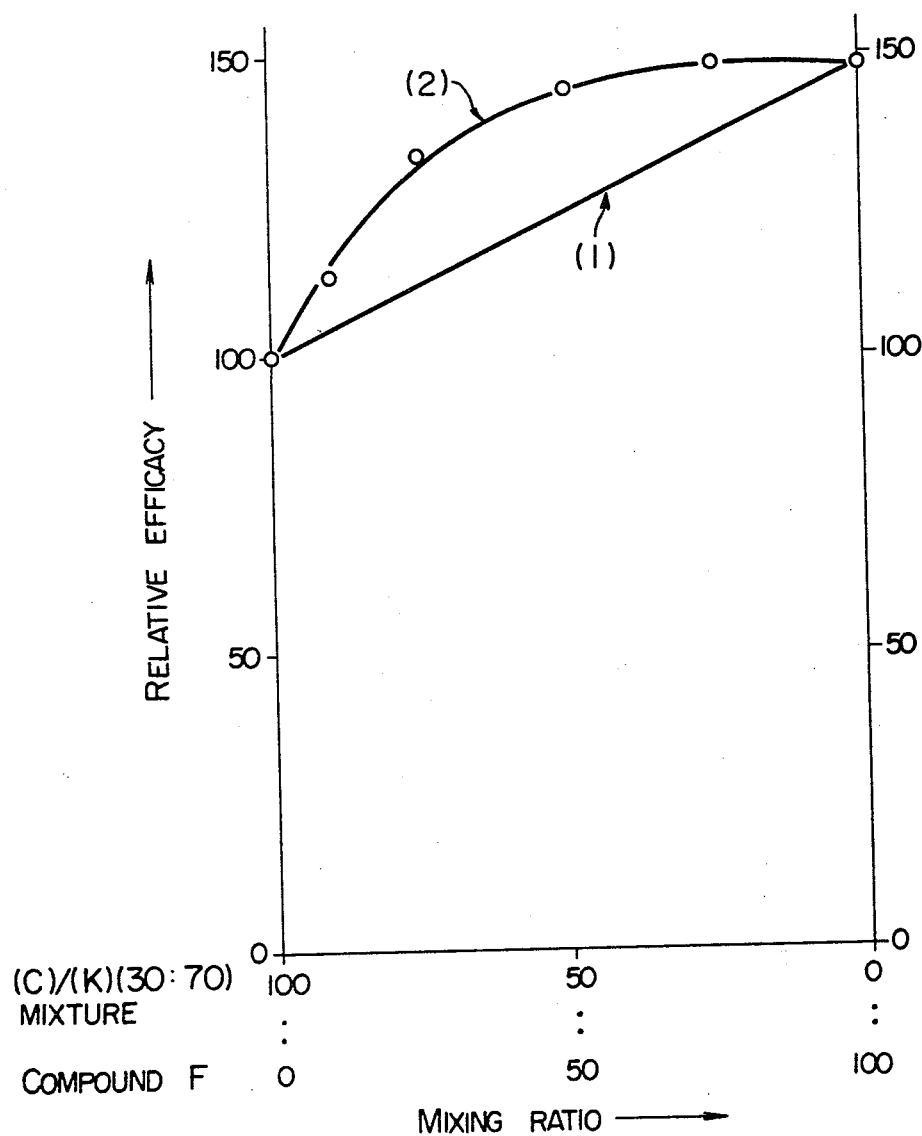
FIG. 1 shows the mortality (relative efficacy) of the (C)/(K)/(F) mixture on housefly, respectively, in a relative efficacy-mixing ratio graph.
Figure 2:
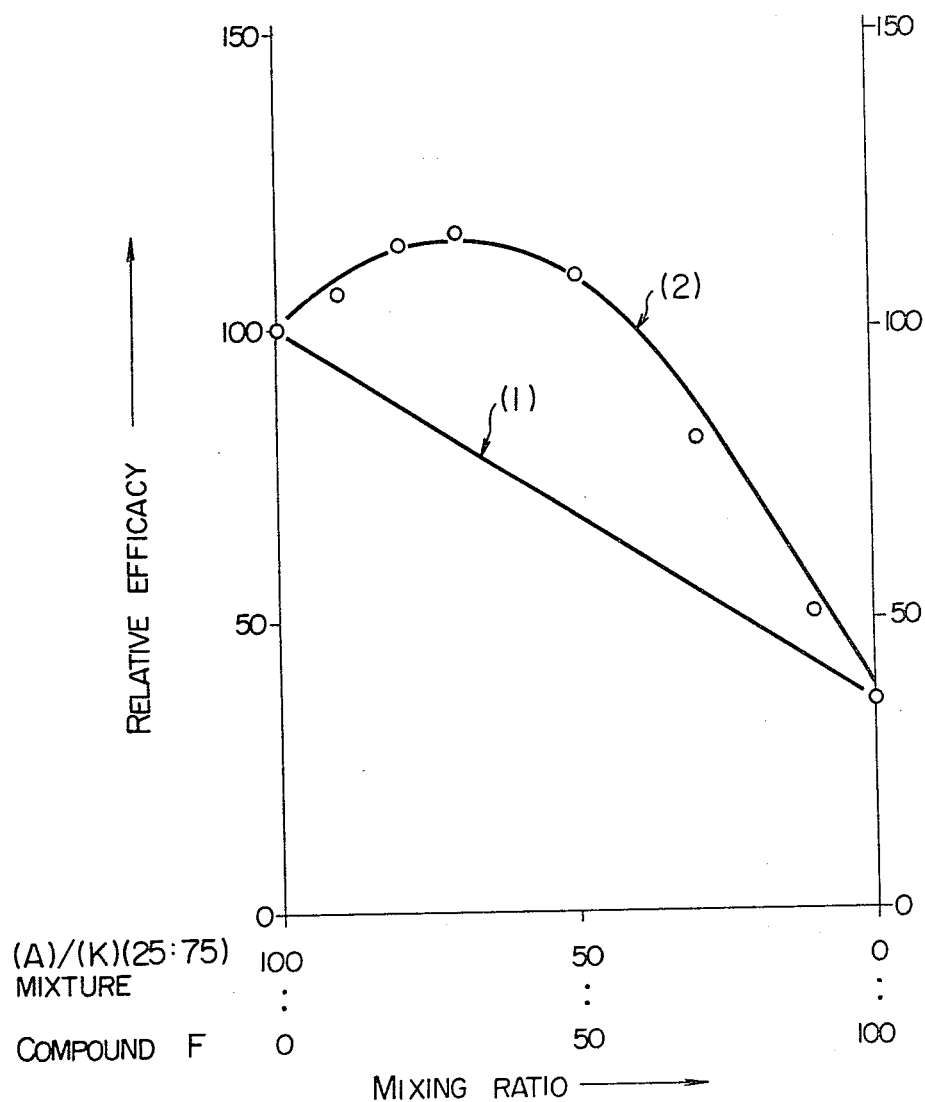
FIG. 2 shows the knock-down effect (relative efficacy) of the (A)/(K)/(F) mixture on Northern house mosquito, in a relative efficacy-mixing ratio graph.
Figure 3:
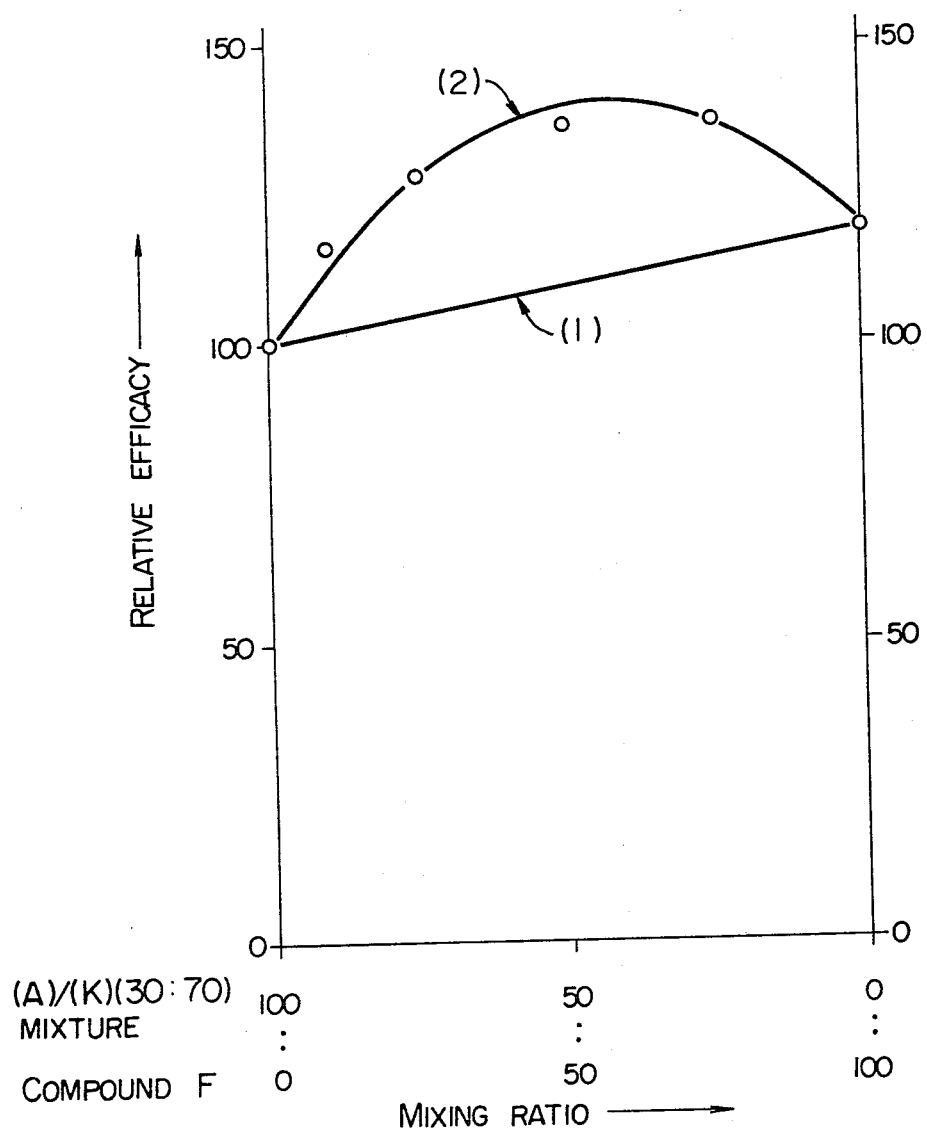
FIG. 3 shows the mortality (relative efficacy) of the (A)/(K)/(F) mixture on German cockroach, in a relative efficacy-mixing ratio graph.

What is claimed is:

1. An insecticidal composition which contains an inert carrier and, as active ingredient, an insecticidally effective amount of a mixture comprising a pyrethroid series compound of the formula (I),

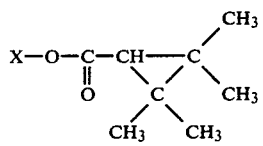

wherein X is

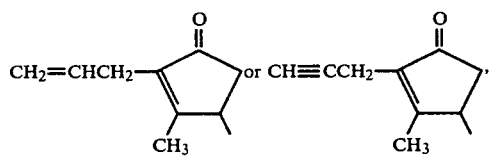

a pyrethroid series compound of the formula (II),

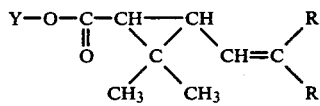

wherein when Y is

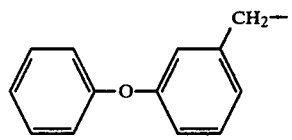

R is a methyl group or chlorine atom, and when Y is

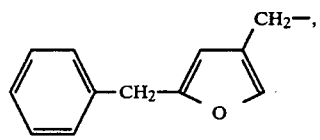

R is a methyl group, and a pyrethroid series compound of the formula (III),

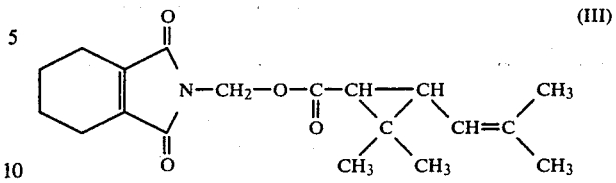

wherein a mixture of (I) and (III) in a ratio of 95:5 to 5:95 is mixed with (II) in a ratio of 90:10 to 40:60.

2. An insecticidal composition according to claim 1, wherein the total concentration of the pyrethroid series compounds is 0.01 to 90% by weight based of the composition.

3. An insecticidal composition according to claim 1, wherein the compound (I) is (+)-2-allyl-3-methylcyclopento-2-ene-1-one-4-yl 2',2',3',3'-tetramethylcyclopropanecarboxylate.

4. An insecticidal composition according to claim 1, wherein the compound (I) is (+)-2-propargyl-3-methylcyclopento-2-ene-1-one-4-yl 2',2',3',3'-tetramethylcyclopropanecarboxylate.

5. An insecticidal composition according to claim 1, wherein the compound (II) is 3-phenoxybenzyl (+)-cis,trans-chrysanthemate.

6. An insecticidal composition according to claim 1, wherein the compound (II) is 3-phenoxybenzyl (+)-trans-chrysanthemate.

7. An insecticidal composition according to claim 1, wherein the compound (II) is 5-benzyl-3-furylmethyl (+)-cis,trans-chrysanthemate.

8. An insecticidal composition according to claim 1, wherein the compound (II) is 5-benzyl-3-furylmethyl (+)-trans-chrysanthemate.

9. An insecticidal composition according to claim 1, wherein the compound (II) is 3-phenoxybenzyl (+)-trans-2'2'-dimethyl-3'-(2'',2''-dichlorovinyl)cyclopropane-1'-carboxylate.

10. A method of knocking-down and killing harmful insanitary insects which comprises contacting the insects with an insecticidal composition according to claim 1.

11. A method of knocking-down and killing harmful insanitary insects according to claim 10, wherein the insects are houseflies, mosquitoes and cockroaches.

12. A method of flushing-out cockroaches which comprises contacting the insect with an insecticidal composition according to claim 1.

* * * * *